United States Patent [19]

Mestas et al.

[11] Patent Number: 4,702,248

[45] Date of Patent: Oct. 27, 1987

[54] APPARATUS FOR GENERATING HIGH FREQUENCY SHOCK WAVES PROVIDED WITH A SCREEN WHICH REDUCES THE ELECTRIC LEAKAGES

[75] Inventors: Jean-Louis Mestas; Dominique Cathignol, both of Lyons, France

[73] Assignees: Technomed International, Paris; Institut National de la Sante et de la Recherche Medicale, Lyons, both of France

[21] Appl. No.: 872,957

[22] Filed: Oct. 27, 1987

[30] Foreign Application Priority Data

Jan. 31, 1986 [FR] France ................................ 86 01381

[51] Int. Cl.$^4$ .............................................. A61B 17/00

[52] U.S. Cl. .................................................... 128/328

[58] Field of Search ............. 128/328, 24 A; 361/232, 361/229, 230

[56] References Cited

U.S. PATENT DOCUMENTS 2,559,227 7/1951 Rieber .

3,537,542 11/1970 Dubois .

3,660,656 5/1972 Frank et al. .................... 361/229 X 3,942,531 3/1976 Hoff et al. .

3,970,076 7/1976 Hepp .

4,507,373 3/1985 Tsilibes ........................... 361/229 X 4,608,983 9/1986 Muller et al. .

FOREIGN PATENT DOCUMENTS 2247195 5/1975 France .

*Primary Examiner*—Michael H. Thaler

*Attorney, Agent, or Firm*—Stiefel, Gross, Kurland & Pavane

[57] ABSTRACT

An apparatus for generating high frequency shock waves having a truncated ellipsoidal reflector is provided. The apparatus has a cavity which constitutes a chamber for reflecting shock waves, the chamber being filled with a dielectric liquid such as water or oil. The apparatus also has a shock wave generator device which generally has two electrodes and a source for selectively and substantially instantaneously providing an electric voltage to the electrodes. The equipotential screen is fast with the ellipsoidal reflector and is grounded by the support formed by the ellipsoidal reflector. This equipotential screen limits electric leakage and thus renders the apparatus safer in operation for destroying targets such as tissues, biliary concretions, kidney stones, etc.

4 Claims, 1 Drawing Figure

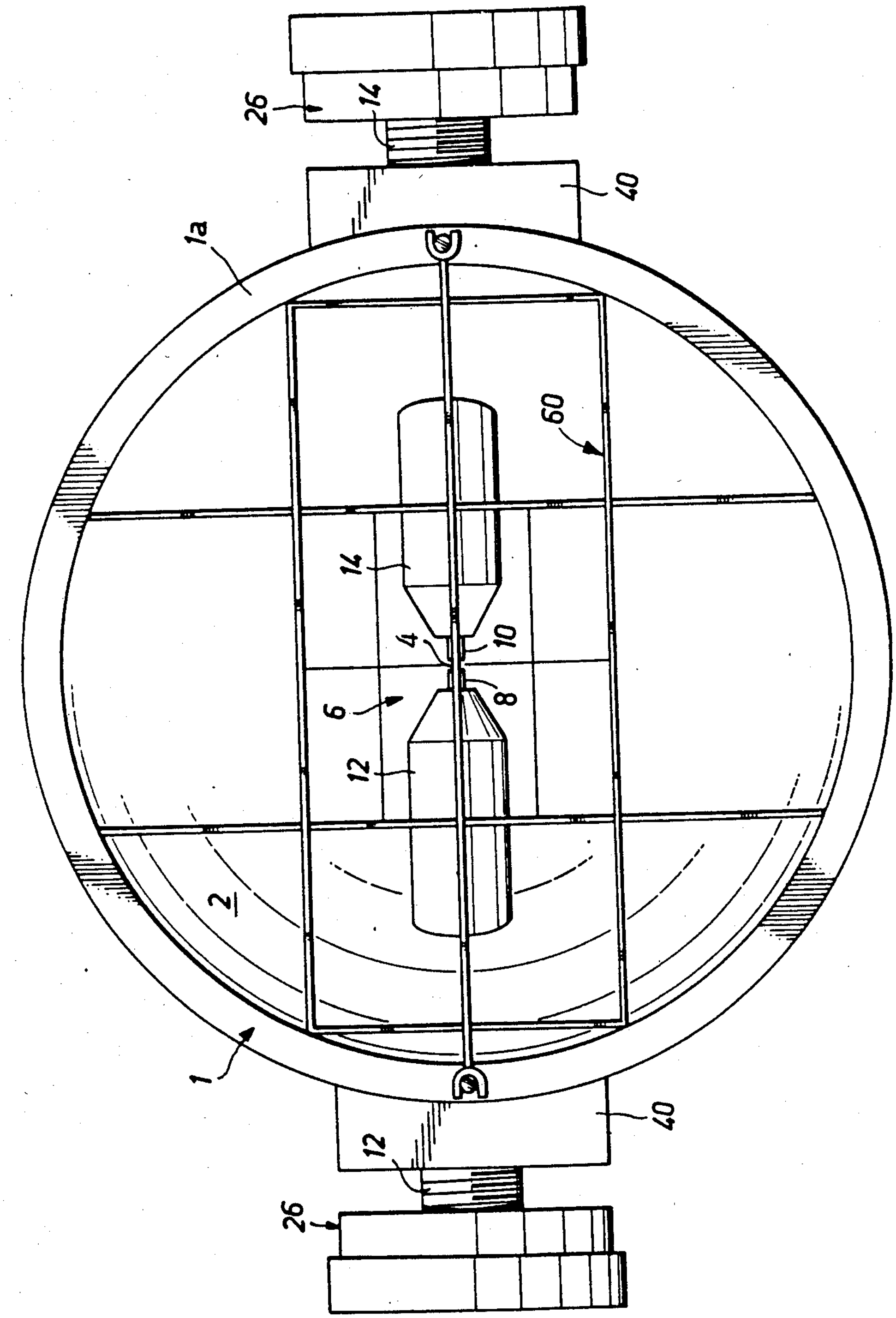
26
14
40
1a
60
14
4
10
8
6
12
2
1
40
12
26

APPARATUS FOR GENERATING HIGH FREQUENCY SHOCK WAVES PROVIDED WITH A SCREEN WHICH REDUCES THE ELECTRIC LEAKAGES

The present invention relates to an apparatus for generating high frequency shock waves and to the use thereof for destroying targets such as tissues, biliary concretions, kidney stones, etc . . . The apparatus is provided with a screen which reduces electric leakages.

U.S. Pat. No. 2,559,227 to RIEBER discloses an apparatus generating high frequency shock waves, comprising a truncated ellipsoidal reflector for reflecting the shock waves, comprising a cavity constituting a chamber for reflecting said shock waves of the same truncated ellipsoidal form, at least one of the two focal points of the ellipsoid being within said chamber opposite the truncated part, said chamber being filled with a liquid for transmitting the shock waves, for example an oil, a shock wave generator device, usually comprising two electrodes, at least partly disposed inside said chamber, with said two electrodes arranged to generate an electric discharge or arc at said focal point located in said chamber opposite said truncated part, and means for selectively and instantaneously delivering an electric voltage to said two electrodes provoking said electric discharge or arc between said electrodes thus generating said shock waves in said liquid contained in said chamber (cf. FIG. 3 and col. 7, line 51 to col. 9, line 30).

RIEBER maintains the chamber closed by the presence of a membrane. The electrodes are made of a highly conductive material such as copper or brass and are mounted on an insulator which is supported as a cantilever with the aid of a connector device so as to adjust the spacing therebetween (cf. col. 4, lines 42 to 53, and col. 8, lines 40 to 47).

A source of electrical energy is provided, particularly a battery, selectively supplying a transformer and a condenser (cf. col. 5, line 64 to col. 6, line 26). This condenser may be charged up to a voltage of 15000 V in order selectively to generate the electric arc or discharge between the electrodes at determined intervals (col. 9, lines 7 to 9 and 24 to 27).

The range of voltage applied and the size of the condenser depend on the nature of the use envisaged (col. 9, lines 27 to 29). This apparatus is used in the medical domain in particular for the destruction of tissues (extracorporal lithotripsy) (cf. col. 3, lines 30 to 64). This apparatus may also be used for the exploration or stimulation of various parts of the nervous system (col. 3, lines 65 to 74).

When shock waves are generated at a focal point of the ellipsoid by the formation of an electric arc between the electrodes, these shock waves are transmitted by the dielectric liquid, reflected by the ellipsoidal wall of the chamber and focused at the other focal point of the ellipsoid which must merge with the target to be destroyed (tissues or concretions).

The positioning of the target at the focal point opposite the one where the electrodes are disposed is of course obtained by any auxiliary locating means.

French Pat. No. 2,247,195 also describes a similar apparatus in which the liquid is constituted by water (page 3, lines 23-24).

When the RIEBER or like apparatus is used, it has been observed that the discharge at electrode level is accompanied by a temporary modification of the potentials and lines of current above the truncated ellipsoidal reflector which may be assimilated to some extent with a semi-ellipsoid.

The principal cause of this phenomenon is the sudden appearance of a high potential (generally between 12000 and 20000 volts) on one of the electrodes with respect to the other.

During experiments made in vivo on dogs, the inventors discovered the importance of the distribution of the lines of current created during the discharge of the condenser between the electrodes.

These lines of current were demonstrated by the application of an alternating voltage at the terminals of the electrodes and the measurement of the differences in potential between a fixed point close to the ellipsoid and points located in the chamber or vessel of the ellipsoid.

It has thus been discovered that it is imperative to reduce the electric leakages in the upper space of the truncated ellipsoidal reflector with a view to improving the patient's safety. It is therefore an object of the present invention to solve the new technical problem consisting in providing a solution for reducing the electric leakages in the upper space of the truncated ellipsoidal reflector, thus improving the patient's safety.

This technical problem is preferably solved in a particularly simple manner in order to avoid complicating the operation of the apparatus or the maintenance thereof.

In fact, it has also been demonstrated that it is possible to reduce the electric leakages in the upper space of the ellipsoidal reflector by the use of insulating liquid such as oils. However, the use of an oil as coupling liquid between the ellipsoid and the patient cannot be envisaged in practice due to the problems of asepsis and of propagation of the waves in the medium. RIEBER uses an auxiliary oil recirculation circuit. It has also been demonstrated that the use of a fine insulating membrane closing the ellipsoidal receiver also leads to a reduction in the electric leakages in the upper space of the ellipsoidal reflector. However, in practice, it is difficult to degas a liquid volume perfectly and air bubbles may occur in its hermetic volume at the moment of the shots. This gaseous volume will then constitute a screen to the pressure waves.

The present invention makes it possible to solve the technical problem set forth hereinabove in a particularly simple manner, without modifying the operational conditions of the apparatus (maintenance, but, on the contrary, the invention improves the patient's safety.

The invention therefore relates to an apparatus for generating high frequency shock waves, comprising a truncated ellipsoidal reflector for reflecting the shock waves, comprising a cavity constituting a chamber for reflecting said shock waves of the same truncated ellipsoidal form, at least one of the two focal points of the ellipsoid is disposed in said chamber opposite said truncated part, said chamber being filled with a dielectric liquid for transmitting the shock waves, for example water or an oil, a shock wave generator device, conventionally comprising two electrodes, disposed at least partly inside said chamber, with said two electrodes arranged to generate an electric arc or discharge at said focal point lying in said chamber opposite said truncated part, and means for selectively and substantially instantaneously delivering an electric voltage to said two electrodes provoking said electric arc or discharge between said electrodes and the generation of said shock waves in said liquid at said focal point, characterized in that an equipotential screen is applied on said truncated part, being fast with the ellipsoidal reflector and directly connected to earth by its support formed by the reflector itself.

According to a preferred embodiment, this equipotential screen is constituted by a metal grid comprising more or less close meshes as a function of the desired attenuation of the electric leakages.

If the positive electrode is partially insulated with respect to the ellipsoidal reflector, the surface of the projecting electrode is then very large and lines of current escape in all directions. This point explains considerable pulse-like leakage currents.

According to another preferred feature of the invention, the positive electrode is virtually completely insulated, which makes it possible to considerably reduce the leakage currents, and therefore the potentials outside the ellipsoidal reflector. The ground electrode is advantageously also insulated virtually completely. Such virtually complete insulation of the ground electrode partially increases the outside potentials above the ellipsoid but offers the important advantage of concentrating the lines of current between the two tips of the electrodes, resulting in improved generation of the electric arc. The limitation of the electric leakages obtained by the screen according to the invention also ensures operation of the apparatus under better conditions of safety, which is essential in the medical field. It presents the advantage of allowing the shock wave to pass without attenuating it, as well as the air bubbles which may possibly be formed in the chamber of the reflector.

The invention will be more readily understood on reading the following description with reference to the accompanying drawings, in which:

The single FIGURE shows, simply by way of illustration and without limiting the scope of the invention, the presently preferred embodiment of the apparatus according to the invention, a plan view of the truncated part of the ellipsoidal reflector disposed vertically as in the case of the ellipsoidal reflector of FIG. 3 of U.S. Pat. No. 2,559,227 to RIEBER. This FIGURE is identical to FIG. 1 of Copending patent application Ser. No. 872,961 filed on June 11, 1986, and owned by the assignee of this invention.

Referring now to the drawing, the single FIGURE shows an apparatus for generating high frequency shock waves according to the invention, of the type generally described by RIEBER in U.S. Pat. No. 2,559,227 with particular reference to FIGS. 1 to 3. The apparatus according to the invention comprises a truncated ellipsoidal reflector, disposed vertically, bearing general reference 1, for reflecting the shock waves having the form shown by RIEBER in FIGS. 1 and 3 of U.S. Pat. No. 2,559,227 or the general form shown in FIG. 3 of French Pat. No. 2 247 195.

This truncated ellipsoidal reflector 1 comprises a cavity 2 constituting a chamber for reflecting the shock waves, having the same truncated ellipsoidal form. At least one focal point, symbolized by reference 4, of the two focal points of the ellipsoid 1 is disposed in chamber 2. The ellipsoidal reflector is made of brass.

It is seen that, according to the embodiment of FIG. 3 of U.S. Pat. No. 2,559,227 to RIEBER, the two focal points of the ellipsoid lie in the chamber whilst, according to the embodiment of FIG. 3 of French Pat. No. 2 247 195, only one focal point is contained in the ellipsoid, the other focal point lying outside the chamber.

A shock wave generator device, generally designated by reference 6, is present and conventionally comprises two electrodes 8, 10. This device 6 is disposed at least partly inside chamber 2 with the two electrodes 8, 10 arranged to generate an electric arc or discharge at the focal point 4 lying in the chamber opposite the truncated part 1*a*. Means (not shown) are provided to deliver, selectively and substantially instantaneously, an electric voltage to the two electrodes 8, 10, provoking an electric arc or discharge between the electrodes 8, 10 generating high frequency shock waves at focal point 4. This means is conventional and described in U.S. Pat. No. 2,559,227 or French Pat. No. 2 247 195, and generally comprises a power source delivering a high voltage, generally of the order of 12000 to 20000 volts, to a condenser disposed in the electric circuit connecting the electrodes to the power source. The structure of the electrodes is preferably that described in the aforesaid copending patent application Ser. No. 872,961 and which is incorporated herewith by reference.

According to the present invention, the apparatus is characterized in that an equipotential screen 60 is applied on the truncated part 1*a*, being fast with the ellipsoidal reflector 1, and directly connected to earth by its support formed by the ellipsoidal reflector.

According to a preferred embodiment, as shown, this equipotential screen is constituted by a metal grid with more or less close meshes as a function of the desired attenuation of the electric leakages. In the example shown in the accompanying FIGURE, the size of the meshes is approximately to scale 1.

A limitation of the electric leakages is thus obtained, ensuring improved safety of the shots.

The positive electrode is preferably insulated virtually completely, this making it possible to considerably reduce the leakage currents, and therefore the potentials outside the ellipsoidal reflector 1.

Similarly, the ground electrode is advantageously also insulated virtually completely, this partially increasing the outer potentials above the ellipsoidal reflector 1 but making it possible to concentrate the lines of current between the two tips of electrodes 8, 10 and consequently to improve the generation of the electric arc. Such virtually complete insulations of the positive electrode and of the ground electrode are obtained by the structure described in Applicants' the aforesaid copending patent application Ser. No. 872,961. Electrodes 8, 10 are mounted on an electrode-holder element disposed inside an insulating support 12, 14 which are respectively dismountably mounted on an insulating intermediate piece 40 fixed to the ellipsoidal reflector. These electrodes are disposed to be mobile by axial translation with the aid of an advance device 26. All the technical advantages mentioned hereinabove as well as those described in assignee's copending Patent Application mentioned above, are thus obtained.

The dielectric liquid which fills chamber 2 is preferably constituted by water which presents an acoustic impedance similar to that of the tissues of living beings.

The apparatus according to the invention is used in the medical field for the destruction of targets such as tissues, biliary concretions, kidney stones, etc.

What is claimed is:

1. In an apparatus for generating high frequency shock waves, comprising a truncated ellipsoidal reflector for reflecting the shock waves, comprising a cavity constituting a chamber for reflecting said shock waves of the same truncated ellipsoidal form, at least one of the two focal points of the ellipsoid is disposed in said chamber opposite said truncated part, said chamber being filled with a dielectric liquid for transmitting the shock waves, for example water or an oil, a shock wave generator device, conventionally comprising two electrodes, is disposed at least partly inside said chamber, with said two electrodes arranged to generate an electric arc or discharge at said focal point lying in said chamber opposite said truncated part; and means are provided for selectively and substantially instantaneously delivering an electric voltage to said electrodes provoking said electric arc or discharge between said electrodes generating said shock waves in said liquid at said focal point, Wherein the improvement comprises the provision of an equipotential screen applied on said truncated part, being fast with the ellipsoidal reflector and directly connected to earth by its support formed by the ellipsoidal reflector itself.

2. The apparatus of claim 1, wherein the said equipotential screen is constituted by a metal grid having a mesh size preselected to achieve the desired attenuation of the electric leakages.

3. The apparatus of claim 2, wherein the positive electrode is insulated virtually completely with the tip thereof exposed.

4. The apparatus of claim 1, wherein the ground electrode is insulated virtually completely with the tip thereof exposed.

* * * * *